(12) United States Patent
Glaesel et al.

(10) Patent No.: US 10,231,606 B2
(45) Date of Patent: Mar. 19, 2019

(54) METHOD FOR DETERMINING MEASURED DATA FROM THE STOMACH OF A PATIENT

(71) Applicants: Norbert Glaesel, Schnaittach (DE); Rainer Kuth, Hoechstadt (DE); Bernhard Roas, Moehrendorf (DE)

(72) Inventors: Norbert Glaesel, Schnaittach (DE); Rainer Kuth, Hoechstadt (DE); Bernhard Roas, Moehrendorf (DE)

(73) Assignee: Siemens Healthcare GmbH, Erlangen (DE)

( * ) Notice: Subject to any disclaimer, the term of this patent is extended or adjusted under 35 U.S.C. 154(b) by 178 days.

(21) Appl. No.: 15/240,340

(22) Filed: Aug. 18, 2016

(65) Prior Publication Data

US 2016/0353982 A1    Dec. 8, 2016

Related U.S. Application Data

(62) Division of application No. 14/073,170, filed on Nov. 6, 2013, now abandoned, which is a division of application No. 13/056,394, filed as application No. PCT/EP2009/054424 on Apr. 15, 2009, now abandoned.

(30) Foreign Application Priority Data

Jul. 30, 2008   (DE) ........................ 10 2008 035 542

(51) Int. Cl.
    *A61B 1/00*        (2006.01)
    *A61B 1/04*        (2006.01)
    *A61K 9/00*        (2006.01)
    *A61B 1/273*      (2006.01)

(52) U.S. Cl.
    CPC .......... *A61B 1/041* (2013.01); *A61B 1/00158* (2013.01); *A61B 1/2736* (2013.01); *A61K 9/0095* (2013.01)

(58) Field of Classification Search
    CPC .............. A61B 1/00158; A61B 1/041; A61M 2202/04; A61M 2202/0468; A61M 2202/0482; A61K 9/0095
See application file for complete search history.

(56) References Cited

U.S. PATENT DOCUMENTS

| | | |
|---|---|---|
| 4,816,044 A | 3/1989 | Weisert et al. |
| 4,957,112 A | 9/1990 | Yokoi et al. |
| 5,681,260 A | 10/1997 | Ueda et al. |
| 5,695,784 A | 12/1997 | Pollinger et al. |
| 6,946,149 B2 | 9/2005 | Cleveland |
| 2003/0060702 A1 | 3/2003 | Kuth et al. |
| 2003/0202957 A1 | 10/2003 | Cleveland |
| 2004/0111011 A1 | 6/2004 | Uchiyama et al. |
| 2007/0106112 A1 | 5/2007 | Gat et al. |
| 2007/0221233 A1 | 9/2007 | Kawano et al. |
| 2007/0225552 A1 | 9/2007 | Segawa et al. |
| 2007/0260175 A1 | 11/2007 | Segawa et al. |
| 2007/0264732 A1 | 11/2007 | Chen |
| 2009/0171146 A1 | 7/2009 | Fujita |

FOREIGN PATENT DOCUMENTS

| | | | |
|---|---|---|---|
| CN | 1179284 A | 4/1998 | |
| DE | G9305066.6 U1 | 7/1993 | |
| DE | 10326188 A1 | 11/2004 | |
| JP | 01136643 A | 5/1989 | |
| JP | 2006 061213 A | 3/2006 | |
| JP | 2006061213 A * | 3/2006 | ............... A61B 8/12 |
| JP | 2006061213 A | 3/2006 | |
| WO | WO-1991/18612 A1 | 12/1991 | |

\* cited by examiner

*Primary Examiner* — Timothy J Neal
*Assistant Examiner* — Aaron B Fairchild
(74) *Attorney, Agent, or Firm* — Schiff Hardin LLP

(57) ABSTRACT

In a method to obtain measurement data from the stomach of a patient using an endoscope, a degassed aqueous drink solution is administered to the stomach of the patient and the measurement data are acquired with the degassed aqueous drink solution present in the stomach.

5 Claims, No Drawings under the conditions in the stomach is how the liquid used for the expansion is introduced into the stomach. In the ingestion of a liquid, significant quantities of gas—in particular air—are nearly always also introduced into the stomach. The gases enter into solution in the drink solution until reaching a saturation limit predetermined by the conditions in the stomach (temperature, pH value, pressure). Further gas quantities that cannot be dissolved form macroscopic bubbles in the stomach. The reactions already described above can continue to reduce the solubility in the drink solution, such that additional gas that is initially dissolved in the drink solution outgasses.

METHOD FOR DETERMINING MEASURED DATA FROM THE STOMACH OF A PATIENT

RELATED APPLICATION

The present application is a divisional application of Ser. No. 14/073,170, filed on Nov. 6, 2013, which is a divisional application of Ser. No. 13/056,394, filed on Jan. 28, 2011 (now abandoned).

BACKGROUND OF THE INVENTION

Field of the Invention

The invention concerns a method to determine measurement data from the stomach of a patient, of the type wherein an endoscope is used to acquire measurement data in the stomach of a patient and an aqueous drink solution is present in the stomach of the patient. The invention moreover concerns a drink solution for the implementation of such a method.

Description of the Prior Art

As used herein, an endoscope means both a generally known, classical endoscope which is brought into the stomach of a patient with the use of a tube directed through the mouth or nose of the patient, and a capsule endoscope (known for example from DE 101 42 253 C1) that the patient can independently swallow. A drink solution is a liquid provided for use in the field of medicine that is selectively brought into the stomach of a patient with a stomach probe or is administered to the patient for independent ingestion.

An endoscopically implemented examination of the human or animal stomach—a gastroscopy—is part of a routine examination in everyday medical practice. Within the framework of the gastroscopy, different variables, measurement values or samples are taken inside the stomach and provided to a physician or assistant for evaluation. For example, content substances or concentrations of the stomach contents are measured, the chemical composition of the gastric juices are determined or image data of the stomach mucosa are collected.

In classical endoscopy, a tube is directed through the mouth or nose of the patient into his stomach. Since the stomach is a hollow muscle, this is normally expanded by blowing in a gas (for example air or $CO_2$), in particular for the implementation of visual examinations. As a result of this expansion, regions of the stomach that are otherwise covered by the mucosa folds are also accessible.

A variant that is more comfortable and gentle for the patient relative to classical gastroscopy uses a capsule endoscope that can be swallowed. To transfer measurement data from inside the stomach, the capsule endoscope/the endoscopy capsule is connected (for example via a radio connection) with a transmission station placed in proximity to the patient. For targeted acquisition of measurement and/or image data from specific regions of the stomach, the capsule endoscope can be magnetically navigable. This type of capsule endoscopy is also designated as MGCE (magnetically guided capsule endoscopy). For example, a capsule endoscope that is suitable for this method arises from DE 101 42 253 C1, which was already mentioned. In contrast to conventional gastroscopy, in capsule endoscopy the stomach is expanded not with a gas but rather with the aid of a liquid. However, multiple measurement errors have been observed in the acquisition of measurement data.

SUMMARY OF THE INVENTION

An object of the invention is to provide a method to determine measurement data from inside the stomach which is improved with regard to its precision. The invention also encompasses a drink solution for application in such a method that allows an improved accuracy in the measurement value acquisition.

In the method according to the invention an endoscope to acquire the measurement data is present in the stomach of the patient to obtain measurement data from said stomach. During the acquisition of the measurement data, an aqueous drink solution that is previously degassed is present in the stomach of the patient.

As used herein, a degassed drink solution is a drink solution that is free of dissolved gases at least insofar as that gas bubble formation is nearly precluded when this is brought into the stomach of the patient. The conditions prevailing in the stomach of a patient are to be taken into account in this context. The drink solution is thus degassed at least insofar as that this no longer outgasses given the conditions prevailing in the stomach of the patient, for example with regard to temperature, pH value etc. A complete degassing of the drink solution is normally not necessary in this context.

The method according to the invention is based on the following insight.

The expansion of the stomach with the use of a liquid that is particularly advantageous for capsule endoscopy entails different technical problems. However, the following statements apply for both classical endoscopy and capsule endoscopy.

For example, reactions can occur between the liquid used for the expansion and the stomach contents, in particular the gastric juices. The formation of gas bubbles has been observed multiple times in the chemical and/or physical interaction between the liquid and the stomach contents. A gas bubble development inside the stomach has been connected with the occurring measurement errors of the probes present in the endoscope.

A bubble development is particularly critical for the acquisition of optical image data of the stomach mucosa. Finely distributed bubbles dissolved in the liquid used to expand the stomach reduce its optical quality and lead to a high proportion of scattered light in the image data. Moreover, bubbles adhering to the outside of the capsule can cause image errors since the optics used to acquire the image data are entirely or partially covered.

The gas bubble formation inside the stomach is particularly problematic for a magnetically navigable capsule endoscope. For example, an adhesion of gas bubbles to the surface of the capsule leads to unwanted local buoyancy forces that can cause the capsule to tumble but at least significantly hinder its navigability.

In summary, the bubble formation occurring in the stomach could be identified as a primary cause for arising measurement errors. To avoid the gas formation, the drink solution is degassed according to the invention. This measure is motivated by the following considerations.

The drink solution that is transported into the stomach to expand it is in contact with both the stomach contents and the stomach mucosa. After the drink solution has been introduced into the stomach of the patient, various chemical reactions can occur between this and the stomach contents or, respectively, the gastric juices produced by the stomach mucosa. One example is the variation of the pH value of the drink solution due to the (typically acidic) gastric juices. If the pH value drops, the solubility of $CO_2$ in water decreases, such that this outgasses. This and other reactions have been connected with a gas formation inside the stomach. An additional effect that leads to the gas bubble formation inside the stomach is the warming of the drink solution. In that the temperature of the drink solution increases—for example from room temperature or below this to the typical temperature of the stomach—the solubility of the gases present in the drink solution decreases, whereby these escape. In order to suppress the gas bubble formation that has been repeatedly observed, the drink solution is degassed before this is brought into the stomach of the patient. The drink solution is thus freed of dissolved gases at least insofar as that a gas bubble development is nearly precluded if said solution is brought into the stomach of the patient. Particular attention is thereby granted to the gases $CO_2$, $N_2$ and $O_2$. These gases represent the primary components of ambient air and are correspondingly dissolved in drinking water, for example. The drink solution is advantageously predominantly freed of these gases.

The gas bubble development that is suppressed in this manner has an advantageous effect on the precision of the measurement values detected with the endoscope. In conventional measurement methods that use a drink solution that has not been degassed, it has been repeatedly observed that gas bubbles adhere to the sensors of the endoscope and in this way cause severe measurement errors. In particular in the acquisition of optical image data, severe distortions occur in conventional measurement methods. For example, the drink solution can become turbid due to dissolved gas bubbles, such that the image data appear indistinct or exhibit a high proportion of scattered light.

Both the determination of image data from inside the stomach of the patient and the determination of additional measurement data becomes significantly more reliable due to the degassing of the drink solution.

The aqueous drink solution according to the invention that is for use in a measurement method in which this is present in the stomach of a patient in additional to an endoscope for acquisition of measurement data is characterized in that this solution is degassed. As has already been mentioned above, the drink solution is freed of dissolved gases at least insofar as that a gas bubble development is nearly precluded when this is brought into the stomach of the patient.

Significant advantages of the drink solution according to the invention have already been cited in connection with the method according to the invention.

DESCRIPTION OF THE PREFERRED EMBODIMENTS

In the following the invention is explained further using various exemplary embodiments.

To prepare the measurement a degassed drink solution is administered to the patient. The drink solution can be independently taken by the patient, but it can also be brought into his stomach with a probe, for example. The fluid level in the stomach of the patient can be monitored with the aid of ultrasound. In order to compensate for an outflow of the drink solution from the stomach, during the implementation of the measurements drink solution can moreover be additionally drunk by the patient or be brought into his stomach in another manner.

Within the scope of the preparation of the drink solution, according to a first exemplary embodiment this is subjected to a vacuum degassing before it is brought into the stomach of the patient. The vacuum degasing is easily controllable via technical measures and is inexpensive; it can possibly be supported via additional measures for degassing. For example, the drink solution can additionally be heated to expel the dissolved gases.

Osmotic reactions at the stomach wall represent an additional source for the gas bubble formation inside the stomach. According to a further exemplary embodiment, these reactions can be suppressed via an isotonic preparation of the drink solution. The drink solution that is pre-treated in such a manner has the same osmotic pressure as human blood. Osmotic reactions at the stomach mucosa can thus be avoided. The gas bubble development inside the stomach can be prevented or at least can be severely reduced via the reduction or significant avoidance of such osmotic reactions at the stomach wall. The drink solution is preferably prepared isotonically via the addition of sodium chloride, i.e. is compounded with 0.9% by weight of cooking salt.

Among other things, an additional problem in the acquisition of measurement data inside the human or animal stomach is foaming caused by the peristalsis of the stomach. Foam that is present in the stomach in particular hinders the acquisition of optical image data. This applies for both a conventional endoscope and for an endoscopy capsule. In the following reference is made to a capsule endoscope as an example.

The endoscope possesses one or more cameras to acquire image data. In its working position the endoscopy capsule is located at or in proximity to the surface of the drink solution located in the stomach. The endoscopy capsule advantageously possesses multiple cameras, of which a first camera acquires optical data of the stomach mucosa through the drink solution from below the liquid level, for example. An additional camera can be arranged above the liquid level to acquire image data. In particular, the latter is significantly affected by foam formation inside the stomach.

Foam present in the stomach hinders the acquisition of optical image data; however, other sensors that are possibly present at the endoscope can be disrupted by foam present in the stomach. To improve the working conditions of the endoscope inside the stomach, the drink solution is compounded with a defoaming agent, advantageously with a silicone oil. The use of silicone oil is particularly advantageous since this is physiologically harmless; silicone oil is inert inside the body, as is known from silicone implants. The addition of silicon oil produces a reduction of the surface tension of the drink solution provided in the stomach. This leads to a reduction of the foam formation.

As already mentioned, in addition to optical image data the endoscope can also detect additional variables, for example concentrations of specific content substances present in the stomach. One example is the measurement of the ammonia content of the stomach contents. Ammonia exists as both $NH_3$ and $NH_4^+$ in an aqueous environment. The equilibrium between $NH_3$ and $NH_4^+$ shifts depending on the pH value prevailing in the stomach. To determine a significant measurement value of the $NH_3$ concentration it is decisive that the pH value in the stomach of the patient has approximately the same value in every measurement. This in particular applies for a time-dependent measurement of the $NH_3$ concentration. In such a measurement the variation of the $NH_3$ concentration in a certain time period is observed. Such a measurement could be disrupted by the continuously occurring production of gastric juices, for example. For this reason, according to a further exemplary embodiment the drink solution is compounded with a pH buffer. A citric acid-phosphate buffer is advantageously used. Such a buffer (also called a McIlvaine buffer) can be adjusted in a pH range between 2.2 and 8. Its buffer range thus lies in a range of the acid environment of the stomach. A mixture of 0.1 molar citric acid (solution A) and 0.2 molar $NaHPO_4.4H_2O$ solution (solution B) of buffer composition X ml A+(100−X) ml B is designated as a McIlvaine buffer.

By adding a pH buffer, constant conditions can be set in the stomach of the patient. This is also advantageous for the acquisition of optical image data since variations in the index of refraction of the drink solution that are caused by variations of the pH value can be avoided.

As already stated, optimally constant conditions inside the stomach are to be sought for the acquisition of measurement data. This requirement extends not only to the chemical composition of the stomach contents but also to the amount of liquid present in the stomach, for example. In general, a drink solution provided into the stomach remains there only for a relatively short period of time. According to a further exemplary embodiment, the temperature of the drink solution is calibrated essentially to the temperature of the stomach to extend the residence duration. A drink solution that is preheated to approximately body temperature has multiple advantages. On the one hand, temperature-dependent density changes within the drink solution do not occur. Such density changes lead to variations in the index of refraction of the drink solution and thus lead to streak formation in the image data. Moreover, a warm drink solution will drain more slowly from the pylorus into the duodenum than a cold drink solution. The residence duration of the preheated drink solution in the stomach is thus improved.

In addition to classical endoscopy and capsule endoscopy, the possibility moreover exists to use a magnetically navigable capsule endoscope to detect measurement values in the stomach of a patient. The aforementioned measures that largely suppress a bubble formation within the stomach of a patient are in particular relevant when such a magnetically controlled endoscopy capsule is used.

A technical problem which occurs in the use of a drink solution that has not been degassed is that bubbles accumulate on the outside of the endoscopy capsule. The bubbles—which have accumulated in a partial region, for example—lead there to local buoyancy forces at the capsule endoscope, whereby its control is made significantly more difficult. In the worst case, the capsule can start to tumble; in this case a targeted measurement value acquisition is impossible.

The use of a degassed drink solution prevents the situation that bubbles can accumulate at the surface of the capsule endoscope. The capsule endoscope can be navigated without problems. The navigability/mobility of the endoscope capsule inside the stomach can be additionally improved in that a silicone oil is admixed with the drink solution. In addition to the aforementioned effect that the bubble formation is reduced, this has the effect of a lubricant. The friction forces between the capsule endoscope and the drink fluid and between the capsule endoscope and the stomach wall are reduced; the navigability of the capsule is improved.

In order to enable a friction-less workflow of the measurements in the stomach of the patient, the drink solution can be provided with the admixtures and be degassed insofar as this is necessary. Such a prepared drink solution must merely be correspondingly tempered before it is brought into the stomach of the patient. Such a prepared drink solution allows a high workflow in the measurement value acquisition.

With the use of the described measures it can be achieved that the physical and chemical properties of the drink solution achieve optimally constant conditions in the stomach of the patient during the measurement value acquisition. The measurement value acquisition is more reliable and reproducible.

Although modifications and changes may be suggested by those skilled in the art, it is the intention of the inventors to embody within the patent warranted heron all changes and modifications as reasonably and properly come within the scope of their contribution to the art.

We claim:

1. A method for acquiring optical image data from the stomach of a patient, comprising:
   degassing an aqueous drink solution;
   in addition to degassing said aqueous drink solution, also preparing said aqueous drink solution isotonically to give said aqueous drink solution an osmatic pressure that is the same as human blood;
   compounding said degassed aqueous drink solution to also include an anti-foaming agent that reduces peristaltic foam formation at said level of said liquid in the stomach of the patient;
   administering the degassed aqueous drink solution to the stomach of a patient;
   after the degassed aqueous drink solution has been administered to the stomach of the patient, magnetically guiding an endoscope, that comprises a camera having a field of view, in the stomach of the patient to situate the camera below a level of liquid in the stomach of the patient while preventing, by a combination of said degassed aqueous drink solution in the stomach of the patient being degassed, isotonically prepared, and compounded with said anti-foaming agent, formation of bubbles on an exterior surface of the endoscope that would otherwise unpredictably add to buoyancy of the endoscope in said liquid and thereby impede said magnetic guidance of the endoscope in the liquid in the stomach of the patient, or be in the field of view of the camera; and
   operating the camera in the endoscope to obtain optical image data represented as electronic signals in said endoscope.

2. A method as claimed in claim 1 comprising preparing said aqueous drink solution by adding NaCl to produce 0.9% NaCl by weight in said aqueous drink solution.

3. A method as claimed in claim 1 comprising, while acquiring said optical image data from the stomach of the patient, monitoring said level of said liquid in the stomach of the patient and, dependent on the monitoring, controlling administration of the degassed aqueous drink solution to the stomach of the patient with an inflow of the administered degassed aqueous drink solution compensating for an outflow from the stomach of the patient during acquisition of said optical image data.

4. A method as claimed in claim 1 wherein said camera is a first camera and wherein said endoscope comprises a second camera also having a field of view, and
   magnetically guiding said endoscope in the stomach of the patient so that, when said first camera is below said level of said liquid in the stomach of the patient, said second camera is above said level of said liquid in the stomach of the patient, and
   operating said second camera to acquire further optical image data from the stomach of the patient above said level of said liquid,
   with said combination preventing formation of bubbles above and below said level of said liquid in the stomach of the patient, in the respective fields of view of both said first and second cameras.

5. A method as claimed in claim 1 comprising degassing $CO_2$, $N_2$ and $O_2$ from said aqueous drink solution.

* * * * *